US005597950A

United States Patent [19]
Mullen

[11] Patent Number: 5,597,950
[45] Date of Patent: Jan. 28, 1997

[54] SURFACTANT MONITORING BY FOAM GENERATION

[75] Inventor: Ken I. Mullen, Los Alamos, N.M.

[73] Assignee: The Regents of the University of California Office of Technology Transfer, Alameda, Calif.

[21] Appl. No.: 334,164

[22] Filed: Nov. 3, 1994

[51] Int. Cl.[6] .................................................. G01N 37/00
[52] U.S. Cl. ........................ 73/60.11; 73/866; 73/53.01
[58] Field of Search .................................. 73/60.11, 866, 73/53.01

[56] References Cited

U.S. PATENT DOCUMENTS

| | | | |
|---|---|---|---|
| 1,866,296 | 7/1932 | Christmann . | |
| 2,315,983 | 4/1943 | Ross et al. | 73/51 |
| 2,380,679 | 7/1945 | Smith | 73/53 |
| 3,151,061 | 9/1964 | Orr | 208/328 |
| 3,555,885 | 7/1969 | Morales et al. | 73/61.1 |
| 4,084,426 | 4/1978 | Gales | 73/60.1 |
| 4,677,304 | 6/1987 | Camp et al. | 250/577 |
| 4,787,110 | 11/1988 | Barone et al. | 8/158 |
| 4,907,444 | 3/1990 | Marx et al. | 73/60.1 |
| 5,035,139 | 7/1991 | Hoefelmayr et al. | 73/223 |
| 5,094,112 | 3/1992 | Hoefelmayr et al. | 73/861.04 |
| 5,108,655 | 4/1992 | Johns, Jr. et al. | 252/321 |
| 5,320,777 | 6/1994 | Nguyen et al. | 252/358 |
| 5,328,375 | 7/1994 | Rogers et al. | 434/226 |
| 5,375,459 | 12/1994 | Gerke et al. | 73/60.11 |
| 5,450,882 | 9/1995 | Cragun | 141/9 |
| 5,465,610 | 11/1995 | Loisel | 73/60.11 |

FOREIGN PATENT DOCUMENTS 3625817  4/1988  Germany .

OTHER PUBLICATIONS

Calus et al., "A New Stabilizing Index to Correlate Foam Height," AIChE Journal (vol. 21, No. 3)., May 1975, pp. 599–600.
Ohsawa, "Froth–Floating Measurements of Detergent," Journal of Colloid and Interface Science, vol. 94, No. 1, pp. 279–283, Jul. 1983.
Clark et al., "Trans. Faraday Soc.", vol. 44, pp. 7–13, (1948).
Walling et al., "An Improved Apparatus for the Study of Foams," J. Phys. Chem. vol. 56, pp. 989–993, (1952).
Ross et al., "The Inhibition of Foaming. VI, The Transmission of Light By Unstable Foams," J. Phys. Chem., vol. 58, pp. 247–250, Mar. 1954.

Primary Examiner—Hezron E. Williams
Assistant Examiner—Jay L. Politzer
Attorney, Agent, or Firm—Bruce H. Cottrell

[57] ABSTRACT

A device for monitoring the presence or absence of active surfactant or other surface active agents in a solution or flowing stream based on the formation of foam or bubbles is presented. The device detects the formation of foam with a light beam or conductivity measurement. The height or density of the foam can be correlated to the concentration of the active surfactant present.

12 Claims, 5 Drawing Sheets

SURFACTANT MONITORING BY FOAM GENERATION

FIELD OF INVENTION

The present invention relates to a device for analyzing or continuously monitoring surfactants or surface active agents in a solution by generating a foam.

BACKGROUND OF THE INVENTION

Previous techniques for the measuring or monitoring of surfactants included: wet chemical techniques; surface tension measurements; and, measurement of foaming.

In a wet chemical technique, surfactants are typically measured using methylene blue (a cationic dye) and chloroform or benzene. Initially, the methylene blue is added to a solution containing surfactants. A methylene blue/surfactant ion pair is then extracted into the organic phase and measured by absorption spectroscopy. The disadvantages of this method are the generation of hazardous wastes and the difficulty in adapting this technique to a continuous, on-line method.

Surfactants can also be detected by measuring the surface tension of a solution. Several methods can be used, e.g., a tensiometer can measure the surface tension by measuring the resistance to withdrawing a plate or ring from a solution. Also, a pulsating bubble surfactometer has been described and is particularly useful for screening lung surfactants. This device works by measuring the pressure difference across a pulsating bubble interface. Still further, the rate of drops forming and falling off a capillary tube has also been demonstrated as a method for measuring surface tension. While all these methods can provide an accurate measure of surface tension, none can be readily adapted to on-line measurements. Each of the above devices require a stable, vibration free, location to operate and all are more costly than the subject matter of the present invention.

Direct measurement of foaming has also been used to detect surfactants. Among previous devices or techniques for measuring foaming are the following. In a first technique known as the Ross-Miles test (ASTM D1173-53), the solution to be tested drips into a long tube. The height of the foam generated is a measure of the surfactant concentration. This method cannot be used on-line or for continuous measurement. This method has the additional drawback of requiring an operator present during the entire test.

A second technique (German Patent No. 3625817 A1 to Bonsels) involves a device to measure surfactants in washing machines. In this device, a solution is continuously pumped through a chamber and out an overflow. A foam is generated by introducing air under the chamber. The presence of foam is detected by a light beam above the surface of the solution. After the measurement is made a burst of air clears the foam out of the light path and the process begins again. Soap will build up on the windows as no provision for cleaning them is provided. This method gives no quantitative information about the surfactant present. It is not possible to adapt this device to quantitative analysis of the surfactant present. The method only determines if free surfactant is present above a predetermined level. No adjustment for the height of the sensor is used minimizing the flexibility of the instrument.

The third technique, U.S. Pat. No. 1,866,296 by H. J. Christmann, involves bubbling air through a column of liquid for a fixed length of time and measuring the foam and its rate of collapse. Like the Ross-Miles test this method cannot be used for continuous or on-line measurements and requires an operator.

SUMMARY OF THE INVENTION

To achieve the foregoing and other objects, and in accordance with the purposes of the present invention, as embodied and broadly described herein, the present invention provides a method of measuring active surfactant concentration within a solution including introducing a surfactant-containing solution into a container having a sidewall whereby a surface of said surfactant-containing solution is established, introducing a gas under the surface of the surfactant-containing solution with the result that a foam is generated, and, sensing a measurable quantity of said foam above the surface of said surfactant-containing solution, said measurable quantity corresponding to active surfactant concentration. In preferred embodiments, the sensing of a measureable foam quantity is accomplished by use of a light beam and a detector, or by a conductivity sensor.

The present invention further provides a monitoring device including a container for receiving a surfactant-containing solution, said container having a sidewall, an inlet for introducing said surfactant-containing solution into said container, a means for introducing gas within said container at a location beneath a preselected level for said surfactant-containing solution, said gas capable of generating foam from said surfactant-containing solution, an outlet for removing said surfactant-containing solution from said container at a predetermined solution height within the container thereby preventing an excess buildup of said surfactant-containing solution, and, a means for sensing a measurable quantity of said foam within the container.

The present invention still further provides a method of selectively controlling foaming within a surfactant-containing solution including measuring the active surfactant concentration and adding an amount of an agent selected from the group of an anti-foaming agent and a foam generating agent, said amount sufficient to control foaming to a preselected level.

DETAILED DESCRIPTION

Figure 1:
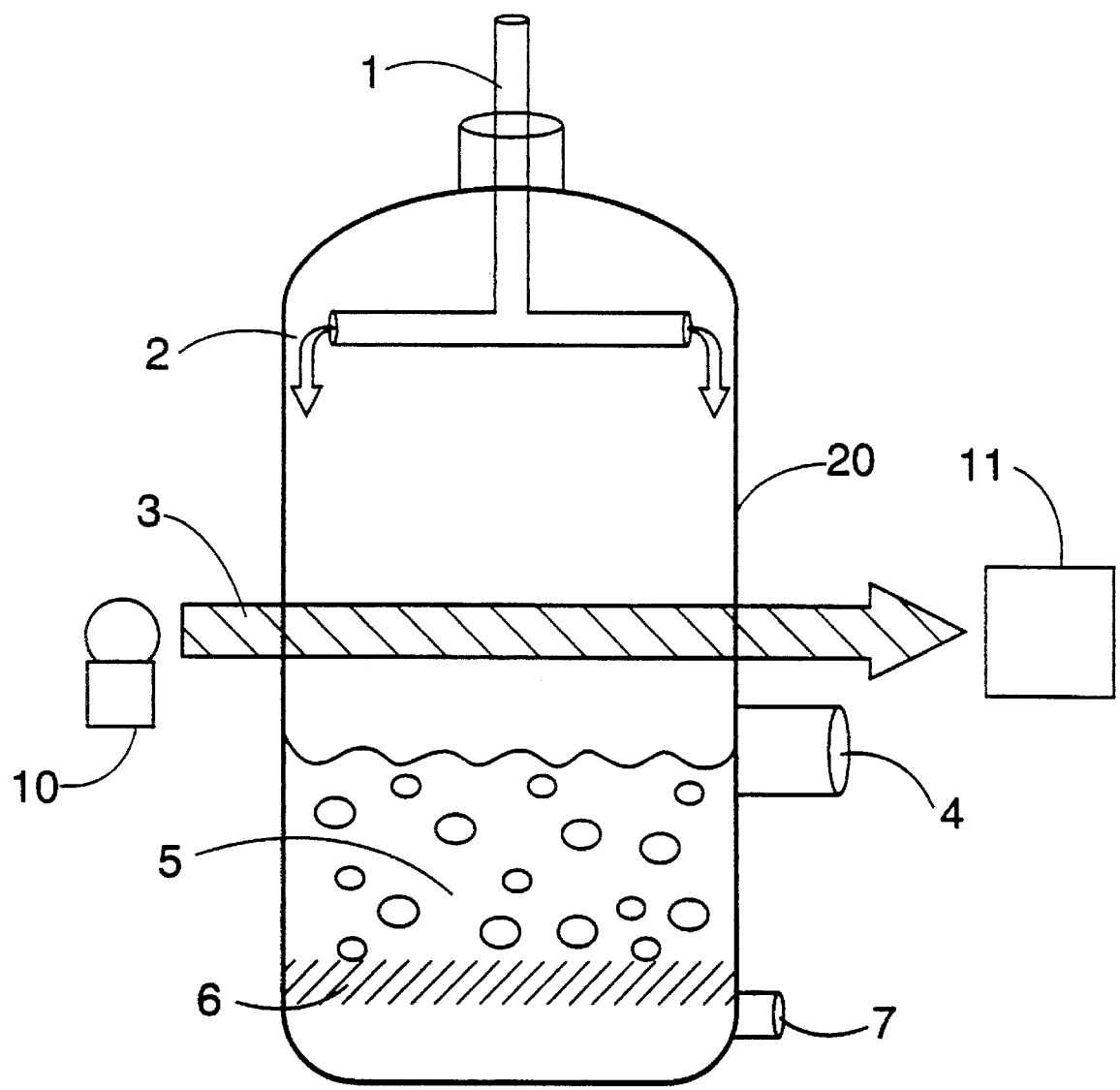
FIG. 1 shows a monitor of the present invention.

An embodiment of the monitor, e.g., the surfactant monitor, is shown in FIG. 1. The solution to be monitored flows in an inlet tube 1. The solution flows out the sides of the inlet tube "tee" 2 and washes the sides of container 20. Container 20 can be cylinder-shaped thus having only a sidewall or can be of a configuration such as a box thus having multiple sidewalls., A light beam 3 is positioned above or optionally through the solution. The light beam can be created by positioning a light source 10 on one side of the container and a detector 11 on, e.g., an opposing side of the container. An overflow 4 maintains a constant liquid level of the reservoir 5. As a means for introducing gas under the surface of solution, a porous glass frit 6 in the bottom of the container 20 can allow air to be pumped into an air inlet 7 to bubble through the reservoir 5. Alternatively, other means for introducing gas under the surface of the solution may be employed such as a stirring means, e.g., a paddle or stir bar, or by other suitable means such as rapidly injecting the incoming solution to be monitored into the solution already in the container thereby agitating the solution hereby causing foaming.

Figure 2:
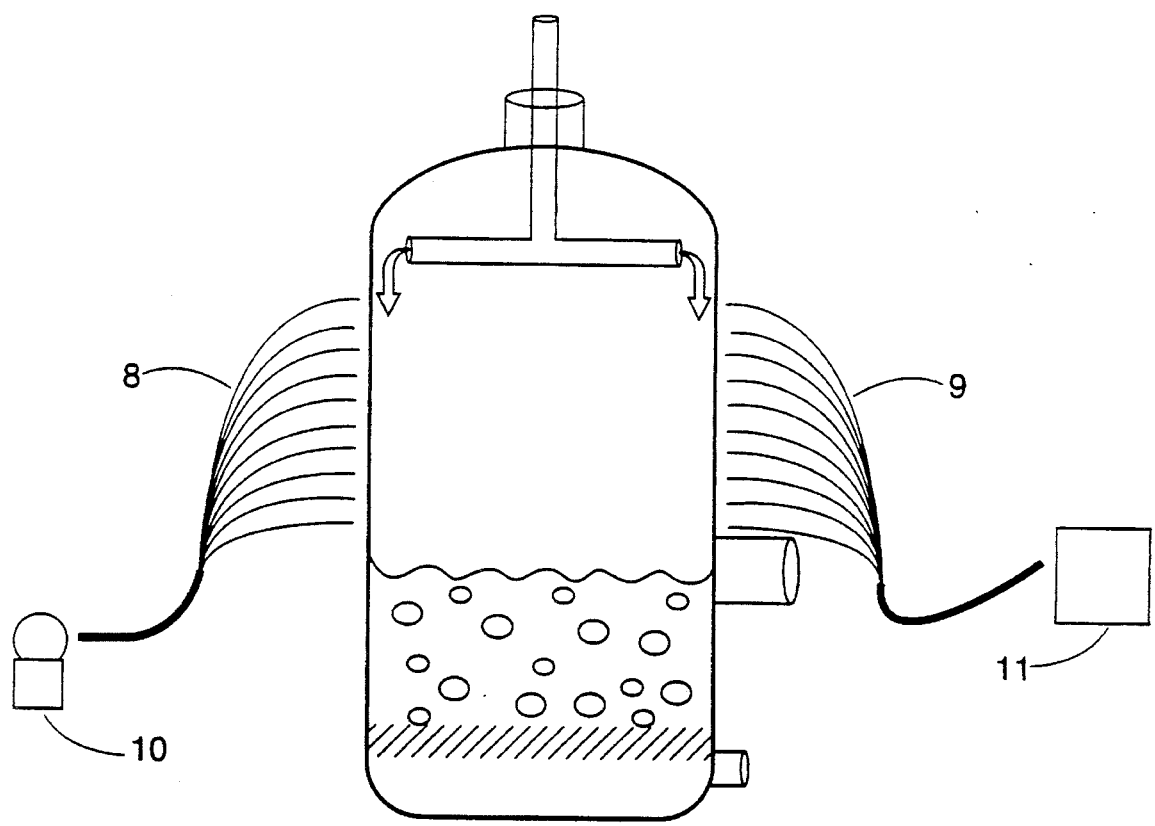
FIG. 2 illustrates the process of optical detection in the present invention.

FIG. 2 shows a typical optical detection of the foam. A light source 10 is introduced into optical fibers 8. The optical fibers can be positioned at any height. Optical fibers 9, on the opposite side of the container, collect light passing through the container. The collected light is measured or detected at the photodetector 11. Any number of optical fibers may be used. Optionally, the light source 10 and the photodetector 11 can be positioned on opposite sides of the container and optical fibers 8 and 9 eliminated.

Figure 3:
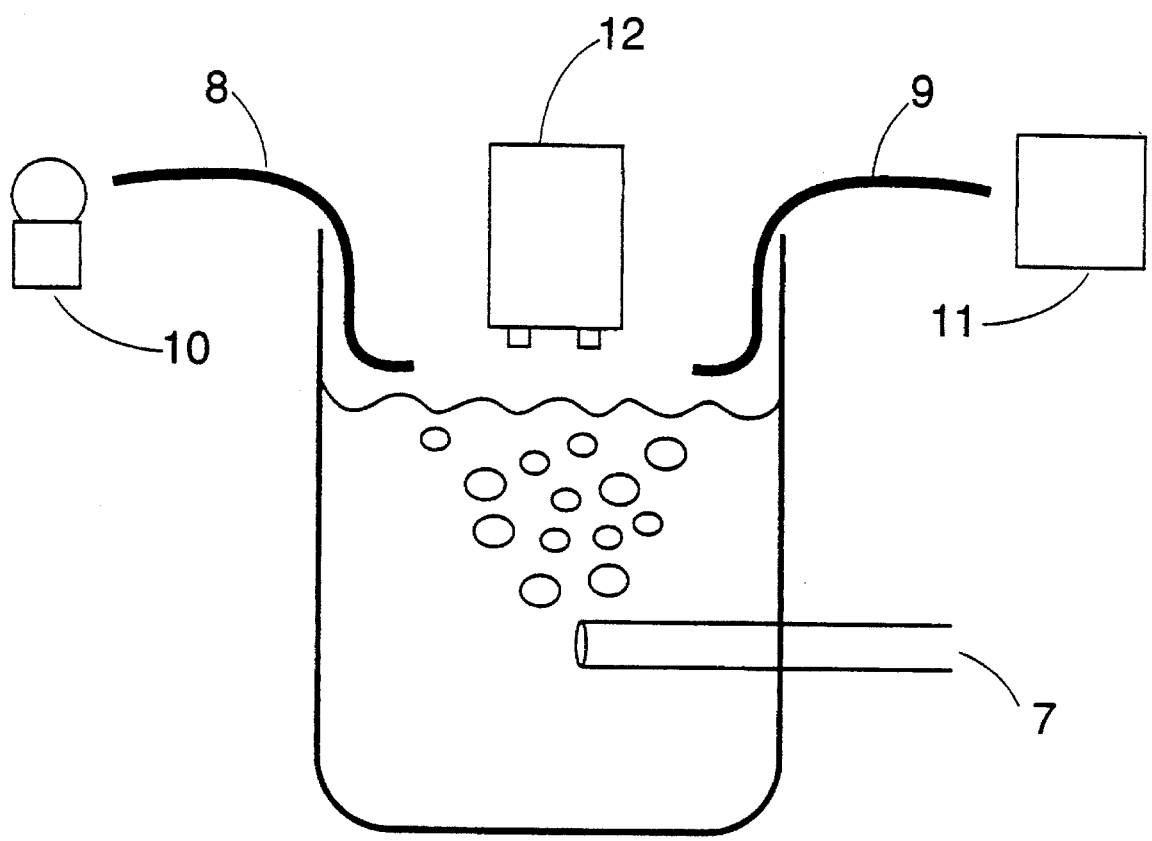
FIG. 3 illustrates monitoring an active surfactant-generated foam layer in an open vessel.

FIG. 3 shows another alternate configuration. A light source 10 is carried by an optical fiber 8. A second optical fiber 9 carries the transmitted light to a photodetector 11. Bubbles or foam are formed either by air introduced under the solution at the air inlet 7 or by the generation of a gas as in $H_2$ or $O_2$ generation at an electrode. Conductivity detector 12 is an alternative to optical detection to sense the presence or height of the foam.

The concentration of active surfactant in a sample or process stream is determined by a measurable quantity of the foam generated, e.g., by the height and/or density of the foam generated. The term "active surfactant" is meant to include any additive that can generate a foam. By the term "measuring surfactant concentration" it is meant either directly measuring or determining surfactant concentration or determining an intermediate foam quantity. The inlet stream can continuously suppress the foam generated and cause the system to reach an equilibrium dependent on the concentration of surfactant. Without the inlet stream the foam would continue to build and would not reach a stable height or density. The foam suppressing effect of the inlet stream allows continuous measurement of the concentration of active surfactant. The inlet of additional solution is preferably above the surface of solution within the container and can be onto a sidewall or directly onto the surface of the solution. A further advantage to such configuration is that the inlet stream can continuously wash the walls of the container. This keeps the optically transmitting windows clean. In contrast, the foam in the device of Bonsels (German Patent No. 3,625,817 A1) is periodically cleared by a burst of air, with this practice resulting in a gradual buildup of surfactant on the optical surfaces.

The device or monitor of the present invention can be used to measure the quantity of active surfactant or surface active agent as a bench top measurement or for continuous monitoring of a process stream or used to measure the foam-generating potential of a given solution. The device can be used to indicate the presence or absence of active surfactant at a predetermined level or used to continuously measure the concentration of active surfactant. The particular method of use depends on the application. For example, the device can be used as an alarm indicating the active surfactant level is too high for discharge to waste or too low for effective cleaning. In the continuous measurement mode, the device can be used to meter in anti-foaming agent or surfactant, when necessary.

The optical and electronics portion of the device can be used to monitor foam height and/or density in an open tank. An example is measuring foam used to suppress mist formation, e.g., in an electroplating bath. The bubbles can be generated by air pumped through a porous frit or by the formation of $H_2$ or $O_2$ gas at the electrodes.

Foam density or height is preferably determined optically. The means for sensing a measureable quantity can generally be an optical sensor or can be a conductivity sensor. In the simplest case, the presence of foam interrupts a light path. The number of interruptions in an elapsed time, as the foam level fluctuates around an average level, can be used to determine the active surfactant concentration. The sensor can be configured to require that the optical path be continuously interrupted for a set time before the sensor outputs that the path is broken. This time delay can be used to smooth out the signal. Adding time delay and optical sensitivity adjustments makes it possible to detect small changes in the surfactant concentration. Similarly, the sensitivity of the optical sensing system can be adjusted so that more or less foam is required for the sensor to output that the light path is broken. Suitable optical and conductivity sensors can include an FX7 sensor available from SUNX, an OMNI-BEAM sensor available from Banner Photoselectric Controls, a Telco sensor or a Skan-a-matic sensor.

Alternately, the density of the foam can be measured. The foam density, at some height, is proportional to the active surfactant concentration. The portion of the light beam that passes through the container depends on the number of interfaces (bubbles) in the path. Therefore, the portion of the beam that passes through the container can be correlated to the concentration of active surfactant.

The height of the optical path can be adjustable. This changes the range of active surfactant concentration the device will measure.

Multiple light paths can be used to measure the foam height or density or some function of both. This can be accomplished by using one or more light sources to drive several optical fibers arranged vertically along the container with a matching row of fibers to carry the transmitted light to a detector. Multiple light sources and detectors can also be used. Generally, the use of multiple light paths has been found to result in a greater dynamic range, i.e., an ability to determine a larger concentration range. Similarly, use of a single light path or source situated at angle theta from the horizontal above the surface of the surfactant-containing solution can improve the dynamic range.

The output from the sensor, e.g., the photodetector, can be electronically totalized or integrated. The integrated or totaled signal is proportional to the concentration of active surfactant. For example, Newport Model P6000 meter modified to totalize an oscillating voltage wherever the light beam was blocked and a Red Lion Model IMD meter can be used to sum the total light beam blocked time or totalize voltage output from the sensor.

It is possible to combine the foam density and height measurements using two or more optical sensors. The outputs of these sensors may be evaluated with multivariate statistics or neural networks to determine the type of surface active agent present.

The optical system can be replaced by a conductivity sensor to detect when the foam reaches a preset height.

Besides changing the height of the optical sensor or conductivity sensor, the sensitivity of the monitor can be adjusted by changing the air flow, the height of solution via the outlet position, the porous frit size (this changes the bubble size), and the rate of flow of the solution into the monitor.

In operation, the basic principle is that by introducing a gas into a solution, active surfactants or surface active agents can be detected by measuring the generation of foam or bubbles. In FIG. 1 the solution to be tested or the process stream to be measured or monitored is introduced through the inlet tube 1. It flows out through the "tee" 2 and washes down the walls of the container. This washing action keeps the transparent walls or windows rinsed and optically transmitting. The in-flowing solution also serves to suppress the foam. This establishes an equilibrium between solution flow, active surfactant concentration, gas flow, and foam height and/or density.

The level of the solution is maintained by the overflow 4. Gas is introduced at the air inlet 7. The gas flows through the porous glass frit 6 where it is divided to form bubbles of uniform size. The bubbles pass through the reservoir 5 and form a foam on the surface of the solution. The height of the foam above the solution or the density of the foam at some level are proportional to the concentration of active surfactant in the reservoir. A light beam 3 is broken or interrupted by the presence of foam. A conductivity meter 12 can be used in place of the light beam 3 as shown in FIG. 3. The concentration of the active surfactant can be determined from the height of the foam, or the density of the foam or both.

There are several methods for measuring the foam as illustrated in FIG. 1–3. In the simplest case the light beam is set at a predetermined height. If the light beam is interrupted, it indicates that there is active surfactant in the solution above some concentration. Similarly, if the beam stops being interrupted, the active surfactant concentration has fallen below some level. On or off time delays can be incorporated to smooth out this signal. The intensity of the light beams 10 or 3, or the sensitivity of the photodetector 11 can be adjusted to require different densities of foam to block the beam. The height of the beams 3, 8, or 9 can be adjusted to sense different levels of active surfactant. Similarly the height and sensitivity of the conductivity meter 12, as shown in FIG. 3 can be adjusted to measure different levels of active surfactant. The gas flow and the solution flow can be adjusted to generate more or less foam from a given concentration of active surfactant.

As shown in FIG. 2 several optical fibers 8 and 9 can be used. This provides an output that is some function of foam density and foam height. An analog signal can be read out of the photodetector 11. This signal is proportional to the concentration of surfactant in the solution. This signal can be integrated or totalized over time. This integrated or totalized signal is proportional to the concentration of active surfactant in the solution or process stream. This can also be used to give a time weighted average of the concentration of active surfactant.

FIG. 3 shows another embodiment of the concept of measuring foam. This device has several applications. In many industries, for example in the electroplating industry, surfactants are used to form a foam on the surface of a tank. The foam can then act as an insulating blanket or can be used to reduce mist and contamination of the air. The configuration shown in FIG. 3 has direct application to monitoring a foam blanket or covering. In this scenario the inflow is not required to suppress foaming. Measuring the concentration of active surfactant is not the object. The object is to add enough active surfactant to maintain a foam blanket of the required thickness.

Surfactants reduce surface tension. This is, in part, why they clean. The foam height will be inversely proportional to the surface tension change effected by the surfactant. In this sense, this device can be used to measure the surface tension of a solution.

The monitor of the present invention provides an easy and efficient way to measure surfactants or surface active agents in a process stream or sample. The device can be fully automated to give an output of active surfactant concentration or can be used as an alarm to signal too much or too little active surfactant.

The present invention is more particularly described in the following examples which are intended as illustrative only, since numerous modifications and variations will be apparent to those skilled in the art.

EXAMPLE 1

The threshold level for sensing by the device shown in FIG. 1 was set with deionized water. The sensing means was positioned at the densest part of the bubbles produced by the air at the surface of the deionized water with no surfactant present. Whenever the light beam was blocked by this amount of foam, the sensor or photodetector would be activated. When the sensor was activated, an attached indicator light would go on and a relay would click.

Figure 4:
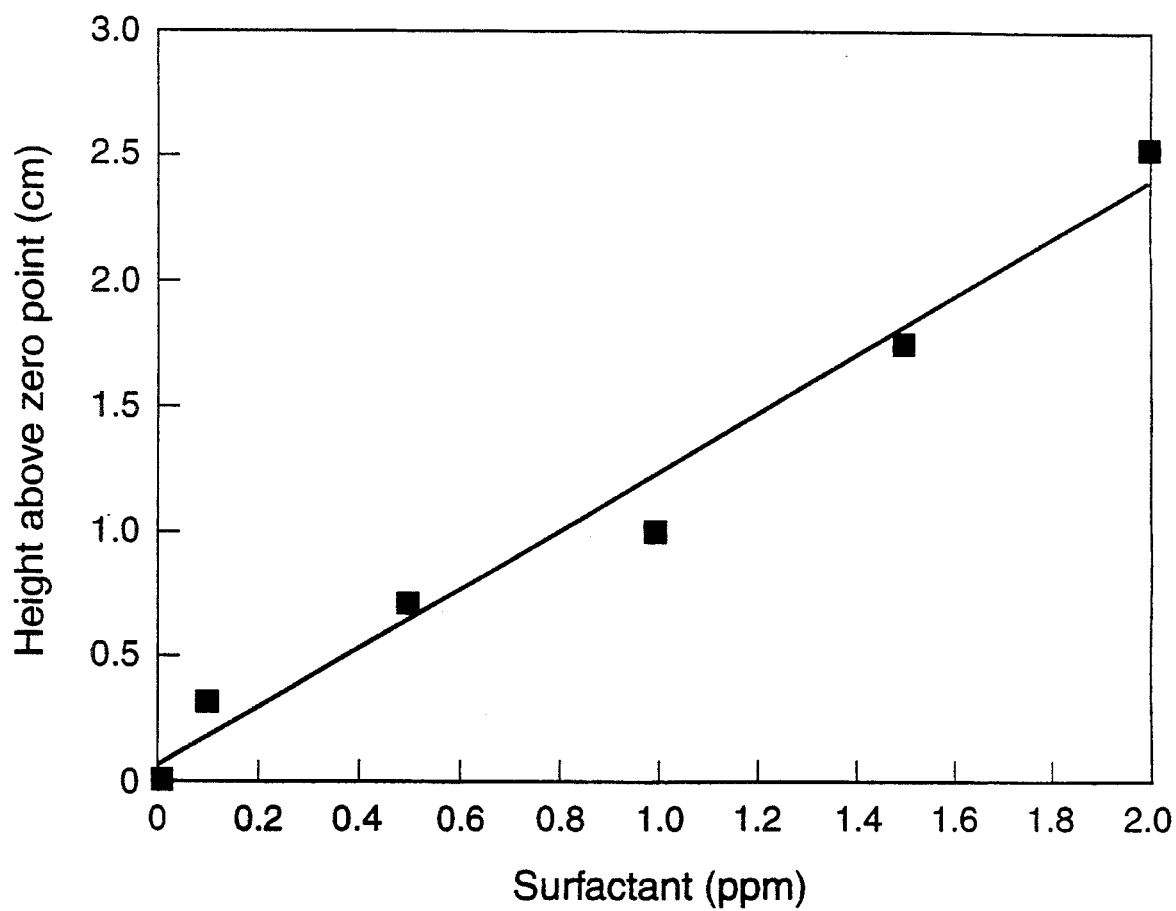
FIG. 4 shows a graph of foam height versus active surfactant concentration.

The device was then used to correlate the height of the optical beam to the concentration of active surfactant. The height of the sensor, i.e., light beam and detector, was initially placed at densest part of the bubbles produced by the air at the surface of the deionized water with no surfactant present and the height recorded. Surfactant was gradually added in small increments and after each small amount of active surfactant was added, the sensor height was adjusted to the height whereat the sensor was continually activated. FIG. 4 presents a calibration curve for BoeNiz alkyl sulfate surfactant, a brightening agent for plating baths available from Pure Coating, Inc. This curve demonstrates that there was a direct linear relationship between the concentration of this surfactant and the foam or bubble height. Naturally, the calibration curve may be different depending on the foaming potential resulting from other constituents of any given solution.

Figure 5:
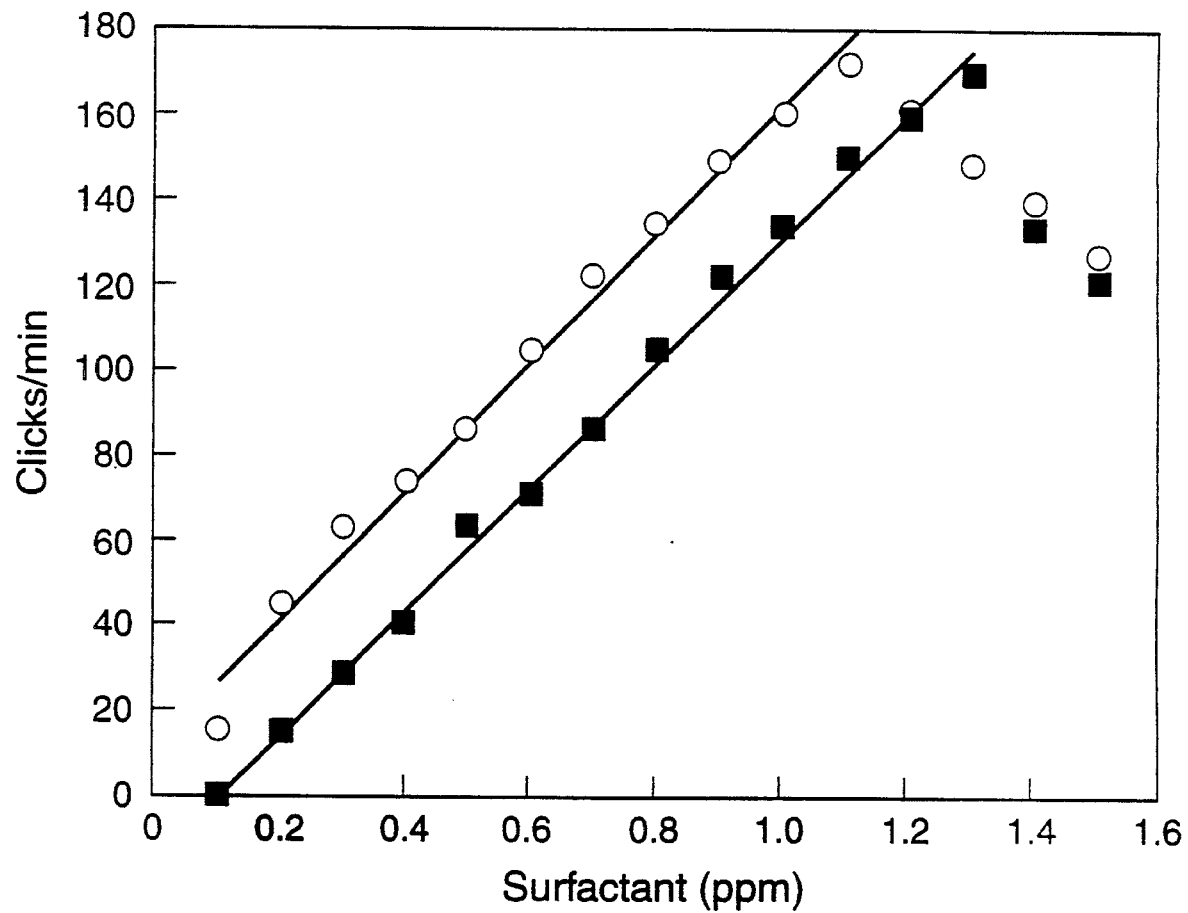
FIG. 5 shows another graph of a foam measurement versus active surfactant concentration.

An alternative operation of the device was then tried. The sensor height was adjusted to the level of the densest bubbles in the deionized water without any surfactant present. The sensor was then raised about 2 millimeters (mm) to a height whereat no activation of the sensor occurred. Surfactant was then added in small amounts as above and the number of activations per minute of the sensor was recorded. As active surfactant concentration increased, the activations or clicks per minute also increased as the light beam was interrupted more often. The number of clicks or sensor activations was used to correlate foam density to the active surfactant concentration. The calibration curves from two different runs with this operation are shown in FIG. 5. Some variability can be noted. This variability results from the difficulty of determining the initial position with deionized water.

Although the present invention has been described with reference to specific details, it is not intended that such details should be regarded as limitations upon the scope of the invention, except as and to the extent that they are included in the accompanying claims.

What is claimed is:

1. A method of measuring active surfactant concentration within a solution comprising:

introducing a surfactant-containing solution into a container having a sidewall whereby a surface of said surfactant-containing solution is established;

introducing a gas under the surface of the surfactant-containing solution with the result that a foam is generated; and, sensing height of said foam above the surface of said surfactant-containing solution by passing at least two light beams horizontally above the surfactant-containing solution into a detector, each light beam at a different vertical distance from the surface of said surfactant-containing solution, said height corresponding to active surfactant concentration, said method further characterized in that said surfactant-containing solution is introduced into said container by continuously passing said surfactant-containing solution downwards upon said sidewall in said container thereby continuously washing the sides of the container and cleaning the optical paths of said light beams.

2. A method of measuring active surfactant concentration within a solution comprising:

introducing a surfactant-containing solution into a container having a sidewall whereby a surface of said surfactant-containing solution is established;

introducing a gas under the surface of the surfactant-containing solution with the result that a foam is generated; and, sensing height of said foam above the surface of said surfactant-containing solution by varying the vertical distance between a sensing device including one or more light beams and the surface of said surfactant-containing solution, said height corresponding to active surfactant concentration, said method further characterized in that said surfactant-containing solution is introduced into said container by continuously passing said surfactant-containing solution downwards upon said sidewall of said container thereby continuously washing the sides of the container and cleaning the optical paths of said light beams.

3. A method of measuring active surfactant concentration within a solution comprising:

introducing a surfactant-containing solution into a container having a sidewall whereby a surface of said surfactant-containing solution is established;

introducing a gas under the surface of the surfactant-containing solution with the result that a foam is generated; and, sensing height of said foam above the surface of said surfactant-containing solution by passing at least two light beams horizontally above the surfactant-containing solution into a detector, each light beam at a different vertical distance from the surface of said surfactant-containing solution, said height corresponding to active surfactant concentration, said method further characterized in that introduction of said surfactant-containing solution into said container is continuously entered into said container in a manner such that the foam height is depressed.

4. The method of claim 1 further including collecting an electronic output signal from said sensing, and determining surfactant concentration by electronically integrating the output signal.

5. A method of selectively controlling foaming within a surfactant-containing solution comprising:

measuring the active surfactant concentration by continuously introducing a surfactant-containing solution into a container having a sidewall whereby a surface of said surfactant-containing solution is established, introducing a gas under the surface of the surfactant-containing solution with the result that a foam is generated, and, sensing height of said foam above the surface of said surfactant-containing solution by passing at least two light beams horizontally above the surfactant-containing solution into a detector, each light beam at a different vertical distance from the surface of said surfactant-containing solution, said height corresponding to active surfactant concentration; and, adding an amount of an agent selected from the group consisting of an anti-foaming agent and a foam generating agent, said amount sufficient to control foaming to a preselected level.

6. A monitoring device comprising:

a container for receiving a solution, said container having a sidewall;

an outlet for continuously removing said solution from said container at a predetermined solution height within the container thereby preventing an excess buildup of said solution;

an inlet situated above the outlet for introducing said solution into said container;

a means for introducing gas within said container at a location beneath a preselected level for said solution, said gas capable of generating foam from said solution in the presence of a foam generating agent within said solution; and, a means for sensing a measurable quantity of said foam within the container, said measurable quantity corresponding to active surfactant concentration within said solution and wherein said inlet for introducing said solution into the container is situated to dispense said solution upon the sidewall of the container whereby continuous dispensing can serve to continuously wash the sidewalls of the container and clean the optical path of one or more light beams.

7. The device of claim 6 wherein said means for sensing said measurable quantity of said foam includes a light source for passing at least one light beam over the surface of the solution within the container and a detector for detecting a light beam.

8. The device of claim 7 wherein the light beam passes horizontally above the surface of the solution into the detector.

9. The device of claim 7 wherein the light beam passes at an angle theta from the horizontal above the surface of the solution into a detector.

10. The device of claim 6 wherein said inlet for introducing said solution into the container is situated to dispense said solution onto the surface of the solution within the container.

11. The device of claim 6 wherein said means for sensing foam height includes a conductivity sensor.

12. The device of claim 6 wherein said means for sensing foam height is adjustably movable upon the sidewall of said container.

* * * * *